(12) United States Patent
Huang et al.

(10) Patent No.: US 9,297,219 B2
(45) Date of Patent: Mar. 29, 2016

(54) UMBILICAL BUCKLING TESTING

(71) Applicant: DMAR ENGINEERING, INC., Houston, TX (US)

(72) Inventors: Zhiming Huang, Missouri City, TX (US); Dagang Zhang, Houston, TX (US)

(73) Assignee: DMAR Engineering, Inc., Houston, TX (US)

( * ) Notice: Subject to any disclaimer, the term of this patent is extended or adjusted under 35 U.S.C. 154(b) by 0 days.

(21) Appl. No.: 14/500,925

(22) Filed: Sep. 29, 2014

(65) Prior Publication Data
US 2015/0260032 A1  Sep. 17, 2015

Related U.S. Application Data

(60) Provisional application No. 61/953,835, filed on Mar. 15, 2014.

(51) Int. Cl.
| | | |
|---|---|---|
| *E21B 7/12* | (2006.01) | |
| *E21B 17/20* | (2006.01) | |
| *E21B 41/00* | (2006.01) | |
| *E21B 47/00* | (2012.01) | |
| *G01N 3/08* | (2006.01) | |
| *G01N 3/20* | (2006.01) | |

(52) U.S. Cl.
CPC ............. *E21B 17/20* (2013.01); *E21B 41/0007* (2013.01); *E21B 47/0006* (2013.01); *G01N 3/08* (2013.01); *G01N 3/20* (2013.01)

(58) Field of Classification Search
CPC ....... E21B 47/0001; E21B 47/01; G01N 3/08; G01N 3/10; G01N 3/12; G01N 3/20
USPC ............................................. 166/336, 250.01
See application file for complete search history.

(56) References Cited

U.S. PATENT DOCUMENTS

| | | | | |
|---|---|---|---|---|
| RE31,993 E * | 10/1985 | Wesch, Jr. | ............. | G01M 3/022 138/90 |
| 4,646,561 A * | 3/1987 | Toelke | .................. | G01M 3/022 73/49.5 |
| 4,793,179 A * | 12/1988 | Carlson | ..................... | G01N 3/12 73/167 |
| 4,905,502 A * | 3/1990 | Gram | ........................ | G01N 3/12 73/167 |
| 5,220,824 A * | 6/1993 | Shelleman | ............... | G01N 3/12 374/57 |
| 5,265,476 A * | 11/1993 | Khachaturian | .......... | G01N 3/08 73/828 |
| 5,419,184 A * | 5/1995 | Pace | ......................... | G01N 3/12 73/49.6 |
| 5,438,863 A * | 8/1995 | Johnson | .................... | G01N 3/08 73/150 A |
| 5,670,708 A * | 9/1997 | Vilendrer | .................. | G01N 3/12 73/37 |
| 5,696,319 A * | 12/1997 | Chung | .................... | G01M 99/00 606/57 |
| 6,343,515 B1 * | 2/2002 | Dodson | ..................... | G01L 5/10 73/831 |
| 6,997,044 B1 * | 2/2006 | Maciejewski | ....... | G01M 3/2846 73/49.5 |
| 7,204,160 B1 * | 4/2007 | Sadegh | ..................... | G01N 3/10 73/862.041 |
| 7,240,569 B2 * | 7/2007 | Foley | ..................... | G01M 5/005 73/862.041 |
| 7,536,921 B1 * | 5/2009 | Chu | ......................... | G01N 3/10 73/760 |
| 8,191,430 B2 * | 6/2012 | Roberts | ..................... | G01N 3/12 73/49.6 |
| 8,522,622 B2 * | 9/2013 | Franklin | .................. | G01N 3/04 73/760 |
| 8,616,230 B2 * | 12/2013 | Studer | ................... | F16K 17/406 137/460 |
| 8,746,042 B2 * | 6/2014 | Sweeney | ................. | B63C 11/42 73/49.1 |

(Continued)

*Primary Examiner* — Matthew R Buck
*Assistant Examiner* — Aaron Lembo
(74) *Attorney, Agent, or Firm* — Liaoteng Wang

(57) ABSTRACT

Apparatus and methods related to umbilical buckling testing are described. For example, some embodiments may contain two damps, a plurality of test fittings, one or more pressure gages, a hydraulic cylinder, and a testing platform, and may be used for testing the umbilical buckling behavior and capacity of an umbilical testing sample.

12 Claims, 2 Drawing Sheets

(56) References Cited

U.S. PATENT DOCUMENTS

| | | | | |
|---|---|---|---|---|
| 2003/0204944 | A1* | 11/2003 | Norek | B21D 26/033 29/421.1 |
| 2005/0252279 | A1* | 11/2005 | Newman | E21B 7/1025 73/49.5 |
| 2010/0206036 | A1* | 8/2010 | Caporusso | B21D 9/073 72/319 |
| 2012/0179392 | A1* | 7/2012 | Zakelj | G01N 3/068 702/43 |
| 2013/0247680 | A1* | 9/2013 | Ota | G01N 3/12 73/788 |
| 2014/0261725 | A1* | 9/2014 | Karamanos | F24F 7/00 137/15.01 |
| 2015/0233805 | A1* | 8/2015 | Huang | G01N 3/20 73/852 |
| 2015/0253228 | A1* | 9/2015 | Kang | G01N 3/20 73/834 |
| 2015/0260032 | A1* | 9/2015 | Huang | E21B 47/01 166/336 |
| 2015/0276570 | A1* | 10/2015 | Kang | G01N 3/20 73/818 |

\* cited by examiner

UMBILICAL BUCKLING TESTING

CROSS REFERENCE TO RELATED APPLICATIONS

This application claims the benefit of U.S. Provisional App. No. 61/953,835, filed on Mar. 15, 2014, which is incorporated herein by reference.

FIELD OF PRESENT DISCLOSURE

This present disclosure relates to umbilical buckling testing.

BACKGROUND INFORMATION

Umbilicals, such as steel tube umbilicals, are commonly used in oil and gas underwater field developments. Umbilical can consist of many tubes, cables, fibers, and fillers, bundled together. In general, an umbilical is specifically designed for each application, and different field applications tend to have different umbilical cross sections. Therefore, different umbilicals have different buckling behaviors and capacities. As they are being used in deeper and deeper water depth, umbilicals are subject to higher and higher compression loads, which can cause the umbilicals to buckle. Umbilical buckling has a number of undesirable effects, such as reduction in flow rate, crack, leak, loss of functionality, or failure of the umbilical tubes. Apparatus and methods can be designed to test the umbilical buckling behavior and capacity so that suitable umbilicals can be designed or selected for various applications by reducing the risks of umbilical buckling and avoiding the undesirable consequences of umbilical buckling.

DETAILED DESCRIPTION

Figure 1:
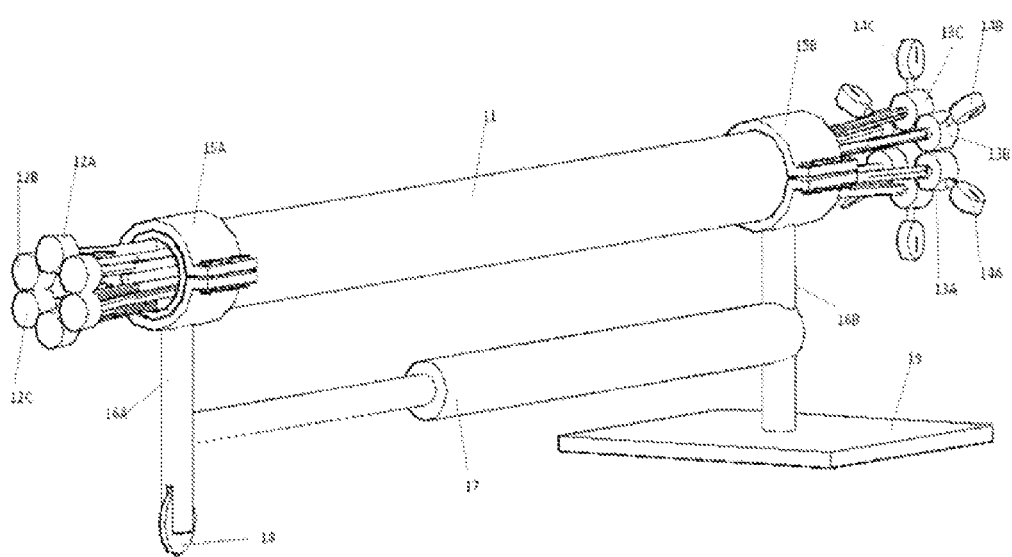
FIG. 1 is a diagram showing the overview of an embodiment of the apparatus and methods for umbilical buckling testing.

This document discloses apparatus and methods related to umbilical buckling testing. FIG. 1 shows a diagram of an implementation of the apparatus and methods for umbilical buckling testing. The umbilical buckling testing for an umbilical testing sample 11 can be performed on a testing platform 19, which can be the ground. The umbilical testing sample 11 can be held in place by two fasteners 15A and 15B, each fastening the umbilical testing sample 11 on one end. The fasteners 15A and 15B can be clamps. The fastener 15B can be fixed to the testing platform 19 through a leg 16B, while the fastener 15A is able to slide freely on the ground through a wheel 18 and a leg 16A, which is further attached to an extendable and retractable arm 17. The extendable and retractable arm 17 can be a hydraulic cylinder. The umbilical testing sample 11 can contain a plurality of tubes, and each tube can be connected to two test fittings, one at each end (shown in FIG. 1 as 12A, 12B, and 12C on one end, and 13A, 13B, and 13C on the other hand, for three tubes). One of the test fittings on each tube can be connected to a pressure gage (shown in FIG. 1 as 14A, 14B and 14C).

Figure 2:
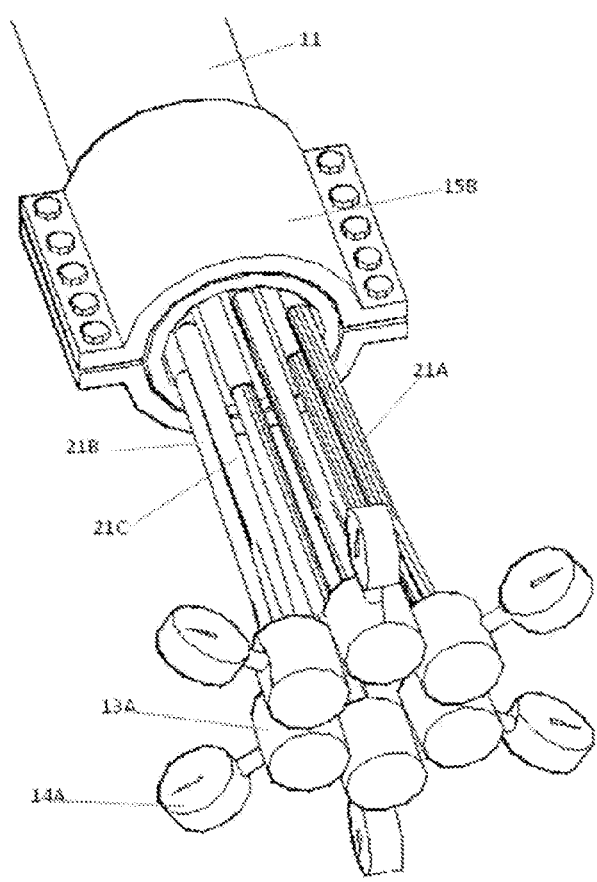
FIG. 2 is a diagram showing the zoomed-in view of the test fitting and pressure gage arrangement of an embodiment of the apparatus and methods for umbilical buckling testing.

FIG. 2 shows the zoomed-in view of the test fitting and pressure gage arrangement of an embodiment of the apparatus and methods for umbilical buckling testing. The individual tubes (e.g., 21A, 21B, and 21C) are stripped out from the umbilical testing sample 11, and mounted to test fittings (e.g., 13A), which are further connected to pressure gages (e.g., 14A).

In some implementations, the testing apparatus can be about five meters in length, two meters in width, and two meters in height. Two clamps can be used to hold the two ends of the umbilical testing sample, and to prevent slippage between adjacent parts of the umbilical testing sample. One of the clamps is fixed to the testing platform, and the other one is able to slide freely. A hydraulic cylinder can be mounted between the two clamps, and can be used to stretch and compress the umbilical testing sample using predefined amplitudes and periods, driven, for example, by a hydraulic pump.

In some implementations, the umbilical buckling testing can be conducted as follows: (i) fasten the ends of the umbilical testing sample with two fasteners (one fastener is fixed on the floor, and the other fastener is supported on the floor but is able to slide freely on the floor, with a hydraulic cylinder connected to the two fasteners to stretch and compress the umbilical testing sample as desired, via its attached fasteners); (ii) mount the test fittings on each individual tube of the umbilical, and fill the tubes with testing fluid, or other appropriate testing materials, depending on the function of the tubes; (iii) pressurize the tubes with predefined pressure value, and monitor the pressure through pressure gages; (iv) activate the hydraulic cylinder to stretch or compress the umbilical testing sample using desired amplitudes and periods; (v) record the umbilical strain and lateral deflection time histories; and (vi) continue moving the hydraulic cylinder to apply either extreme compression loading, or cyclic compression loading, or other desired amplitudes and periods, until one of the tubes leaks, which is monitored through the pressure gage. An abrupt pressure drop shown on the pressure gage may indicate a tube leak or tube failure. The umbilical strain and lateral deflection time histories can be processed to study the umbilical buckling capacity for both extreme compression loading and cyclic compression loading.

Other Embodiments

Various other adaptations and combinations of features of the embodiments and implementations disclosed are within the scope of the present disclosure. For example, the hydraulic cylinders in the present disclosure can be replaced by any of the tensioning devices that can extend and retract in a controllable way. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An apparatus for testing an umbilical containing a plurality of tubes, the apparatus comprising:
   first clamp to secure a first end of the umbilical and allow first ends of the tubes from the umbilical past the first clamp;
   a second clamp to secure a second end of the umbilical and allow second ends of the tubes to extend from the umbilical past the second clamp;

an extendable and retractable arm connected to at least one of the first and the second clamps;

a plurality of test fittings that are mounted on the first and the second ends of the tubes, the tubes capable of being pressurized; and one or more pressure gages that are connected to the test fittings.

2. An apparatus according to claim 1, wherein the first clamp is moveable by an action of the extendable and retractable arm.

3. An apparatus according to claim 2, wherein the first clamp is movable axially by an action of the extendable and retractable arm.

4. An apparatus according to claim 2, wherein the first clamp is fixed to a leg that is movable on a wheel.

5. An apparatus according to claim 4, wherein the leg is attached to the extendable and retractable arm.

6. An apparatus according to claim 1, further comprising a testing platform.

7. An apparatus according to claim 6, wherein the testing platform is connected to the second clamp through a leg fixed on said testing platform, and the leg is further attached to the extendable and retractable arm.

8. An apparatus according to claim 1, wherein the apparatus is about five meters in length, two meters in width, and two meters in height.

9. A method for testing an umbilical containing a plurality of tubes, the method comprising:

fastening two ends of the umbilical with first and second fasteners, wherein:

first ends of the tubes extend from the umbilical past the first fastener;

second ends of the tubes extend from the umbilical past the second fastener;

the first fastener is fixed relative to a floor;

the second fastener is supported on the floor but able to slide freely on the floor; and a hydraulic cylinder is connected to at least one of the two fasteners and capable of stretching and compressing the umbilical desired;

mounting test fittings on the first and second ends of the tubes and filling the tubes with testing fluid or other appropriate testing materials depending on the function of the tubes;

pressurizing the tubes with predefined pressure values and monitor pressures using pressure gauges connected to the test fittings;

activating the hydraulic cylinder to stretch and compress the umbilical using desired amplitudes and periods; and recording umbilical strain and lateral deflection time histories.

10. A method according to claim 9, wherein extreme compression loading is applied using the hydraulic cylinder.

11. A method according to claim 9, wherein cyclic compression loading is applied using the hydraulic cylinder.

12. A method according to claim 9, further comprising continuing moving the hydraulic cylinder using a loading pattern until at least one of the pressures is changed as indicated by a corresponding pressure gauge.

* * * * *